United States Patent [19]
Dabi et al.

[11] Patent Number: 5,221,726
[45] Date of Patent: Jun. 22, 1993

[54] HYDROPHILIC MATERIALS USEFUL IN PREPARING FLUID-ABSORBENT PRODUCTS

[75] Inventors: Shmuel Dabi, Highland Park; Ram L. Kataria, Hamilton Square, both of N.J.

[73] Assignee: McNeil-PPC, Inc., Milltown, N.J.

[21] Appl. No.: 830,444

[22] Filed: Feb. 3, 1992

Related U.S. Application Data

[63] Continuation of Ser. No. 594,255, Oct. 9, 1990, abandoned.

[51] Int. Cl.⁵ .................................. C08J 9/08
[52] U.S. Cl. ...................... 528/93; 521/135; 521/178; 525/523; 528/111; 528/407
[58] Field of Search ............... 528/111, 407, 93; 521/54; 525/523

[56] References Cited

U.S. PATENT DOCUMENTS

| | | | |
|---|---|---|---|
| 4,098,842 | 7/1978 | Login | 525/430 |
| 4,554,297 | 11/1985 | Dabi | 528/111 |
| 4,758,466 | 7/1988 | Dabi et al. | 521/54 |

*Primary Examiner*—Maurice J. Welsh
*Assistant Examiner*—John M. Cooney, Jr.

[57] ABSTRACT

Improved hydrophilic materials, such as foams and films, are provided. These material find use in a wide variety of fluid absorbent products, especially those relating to the absorption of bodily fluids. The soft, absorbent, and resilient foams of this invention exhibit greater wet and dry mechanical strength when compared with those known in the art, as well as improved fluid wicking capacity and lower density. These improved properties are believed attributable to the incorporation into the foams of at least one polyfunctional aliphatic amine.

The provided hydrophilic materials comprise the polymeric reaction product of a mixture which comprises at least one epoxy resin, at least one amine-terminated poly(alkylene oxide), and at least one polyfunctional aliphatic amine. Methods for preparing foams and other hydrophilic materials are also provided. In general, hydrophilic materials are prepared by providing at least one epoxy resin, forming a reaction mixture by contacting the epoxy resin with at least one amine-terminated poly(alkylene oxide) and at least one polyfunctional aliphatic amine, and curing the reaction mixture.

32 Claims, No Drawings

HYDROPHILIC MATERIALS USEFUL IN PREPARING FLUID-ABSORBENT PRODUCTS

This is a continuation of application Ser. No. 594,255, filed Oct. 9, 1990, now abandoned.

BACKGROUND OF THE INVENTION

This invention relates to hydrophilic polymeric materials, to hydrophilic polymers having improved properties, and to the use of such polymers in fluid-absorbent products.

Hydrophilic polymers find extensive use in many applications in the form of foams and films. Hydrophilic foams, for example, can be integral component of sanitary napkins, tampons, diapers, wound and surgical dressings, and other products useful in absorbing bodily fluids. The utility of foams in such applications derives from their high affinity for aqueous liquids.

Unfortunately, the strong interaction between water and many hydrophilic foams often leads to swelling and to a significant loss in mechanical strength. For example, U.S. Pat. Nos. 4,554,297 and 4,508,854, both in the name of the present inventor, Dabi, disclose polymers which are the reaction products of epoxy resins and amine-terminated poly(alkylene oxide). In U.S. Pat. No. 4,554,297, an absorbent foam comprising an epoxy resin and amine-terminated poly(alkylene oxide) oligomers is described. The amine-terminated oligomers in that patent are selected from the group consisting of amine-terminated poly(propylene oxide), amine-terminated poly(ethylene oxide), and mixtures thereof. These polymers were said to contain sufficient amounts of ethylene oxide units to render the polymer hydrophilic. The ratio of ethylene oxide to propylene oxide groups was required to be in the range of 1.0 to 15.0.

While foams made from the polymers disclosed in U.S. Pat. Nos. 4,554,297 and 4,508,854 exhibit the levels of softness, absorbency, and resiliency desired for use in sanitary napkins and other products which absorb bodily fluids, these foams suffer from reduced mechanical strength, particularly when wet. Such loss of mechanical strength tends to compromise the structural integrity of the fluid absorbent products into which these foams are incorporated. Accordingly, there currently exists a need for hydrophilic foams which exhibit acceptable levels of wet mechanical strength.

SUMMARY OF THE INVENTION

The present invention provides improved hydrophilic materials, such as foams and films. The soft, absorbent, and resilient foams of this invention exhibit greater wet and dry mechanical strength when compared with those known in the art, as well as improved fluid wicking capacity and lower density. These improved properties are believed attributable to the incorporation into the foams of at least one polyfunctional aliphatic amine.

The hydrophilic materials of this invention are thus composed of the polymeric reaction product of a mixture containing at least one epoxy resin, at least one amine-terminated poly(alkylene oxide), and at least one polyfunctional aliphatic amine.

This invention also provides methods for preparing foams and other hydrophilic materials. In general, such hydrophilic materials may be prepared by providing at least one epoxy resin, forming a reaction mixture by contacting the epoxy resin with at least one amine-terminated poly(alkylene oxide) and at least one polyfunctional aliphatic amine, and curing the reaction mixture.

Foams may be prepared by providing at least one epoxy resin; forming a prepolymer by contacting the epoxy resin with at least one amine-terminated poly(alkylene oxide); forming a foaming mixture by contacting the prepolymer with at least one amine-terminated poly(alkylene oxide), at least one polyfunctional aliphatic amine, and a blowing agent; and curing the foaming mixture.

Hydrophilic materials comprising the polymers of this invention find use in a wide variety of fluid absorbent products, particularly sanitary napkins, tampons, diapers, wound and surgical dressings, and other products useful in absorbing bodily fluids.

It is thus one object of the present invention to provide hydrophilic polymeric materials.

It is another object to provide hydrophilic polymers having improved properties.

It is yet another object to provide hydrophilic polymers having improved wet and dry strength.

It is still another object to provide hydrophilic polymeric materials useful in the fabrication of fluid-absorbent products.

DETAILED DESCRIPTION OF THE INVENTION

The hydrophilic materials of this invention are composed of the reaction product of a mixture that contains at least one epoxy resin, at least one amine-terminated poly(alkylene oxide), and at least one polyfunctional aliphatic amine.

A wide variety of epoxy resins comprising monomers, polymers, and blends thereof are known in the art. Many are suitable for use in the present invention. Epoxy resins according to this invention should contain, on average, at least about 1.7 epoxy groups per molecule, preferably from about 1.7 to about 4.0 epoxy groups per molecule, and more preferably from about 1.7 to about 2.3 epoxy groups per molecule. The epoxy resin may be a liquid or a low-melting solid. Preferably, the resin is a liquid having a bulk viscosity of from about 200 centipoise to about 2,000,000 centipoise, measured using a Brookfield RVT viscometer at 25° C. The epoxy resin can have an equivalent weight of from about 70 to about 2,000. Those skilled in the art will recognize that epoxy equivalent weight is the gram molecular weight of the resin per epoxy group.

Examples of suitable epoxy resins are polyallyl glycidyl ether, diglycidyl ether of chlorendic diol, the diglycidyl ether of endomethylene cyclohexanediol, epoxy novolac resins, alkanediol diglycidyl ethers, and alkanetriol triglycidyl ethers. Preferred epoxy resins include alkanediol diglycidyl ethers having the formula: wherein n has a value of from 1 to about 25 and X is an alkylene or alkylidene group containing from 1 to about 10 carbon atoms. Preferably, n has a value of from 1 to about 15 and X is alkylene or alkylidene containing from about 2 to about 6 carbon atoms. Preferred alkanediol diglycidyl ethers include ethylene glycol diglycidyl ether, propylene glycol diglycidyl ether, and butanediol diglycidyl ether. More preferred glycidyl ether resins include alkanetriol triglycidyl ethers wherein the alkane group contains from about 2 to about 10 carbon atoms. Even more preferred are glycidyl ether resins wherein the alkane group contains from about 3 to about 6 carbon atoms, such as glyceryl triglycidyl ether and the triglycidyl ether of trimethylolpropane.

While epoxy resins such as these produce soft, absorbent, and resilient foams according to this invention, they tend to react too slowly for use in a commercial process. Thus, where foams are to be provided, the preferred epoxy resins are the di- and polyglycidyl ethers of bisphenols, such as the diglycidyl ether of bisphenol A, which is commercially available from the Shell Chemical Company as EPON 828. The bisphenols from which these resins are prepared should have the formula:

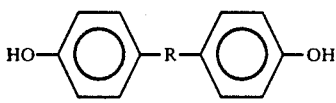

wherein R is a bivalent radical comprising from 1 to about 8 atoms selected from the group consisting of carbon atoms (C), oxygen atoms (O), sulfur atoms (S), or nitrogen atoms (N). Preferably, R is an alkylene or alkylidene group having from 1 to about 8 carbon atoms. More preferably, R is an alkylene or alkylidene group containing from 1 to about 6 carbon atoms. Examples of suitable bisphenols include methylene bisphenol, isopropylidene bisphenol, butylidene bisphenol, octylidene bisphenol, bisphenol sulfide, bisphenol ether, and bisphenol amine. Isopropylidene bisphenol is preferred for preparing hydrophilic foams according to this invention.

The amine-terminated poly(alkylene oxide) may be in the form of mixtures of amine-terminated poly(alkylene oxides), copolymers of alkylene oxides such as random copolymers and block copolymers, or mixtures thereof. Ethylene oxide groups must be present in one or more of the polymers. Preferably, propylene oxide groups are present as well in a ratio of from about 1 to about 15 ethylene oxide groups per propylene oxide group.

The ratio between ethylene oxide groups and propylene oxide groups is important in that a disproportionately large amount of propylene oxide groups will result in a material that is too hydrophobic for use in absorbent products as the absorbent medium. However, a disproportionately large amount of ethylene oxide groups will result in a material that is not sufficiently resilient. The preferred range for this ratio is from about 1 to about 15 ethylene oxide groups per propylene oxide group, more preferably from about 3 to about 10 ethylene oxide groups per propylene oxide group.

Amine-terminated poly(alkylene oxides) are commercially available, one source being the series of polymers sold by the Texaco Chemical Company under the trademark "Jeffamine". A particularly useful series of Jeffamine compounds are designated by Texaco "Jeffamine ED" and have the structure: wherein b has a value of from about 7 to about 50 and the sum of a and c has a value of from about 1 to about 5. These block copolymers are derived from propylene oxide-capped polyethylene glycol and are available from Texaco as compounds wherein the a, b, and c values are in the following ratios:

| Jeffamine Compound | Approximate Value of | |
| --- | --- | --- |
|  | b | a + c |
| ED-600 | 8.5 | 2.5 |

-continued

| Jeffamine Compound | Approximate Value of | |
| --- | --- | --- |
|  | b | a + c |
| ED-900 | 15.5 | 2.5 |
| ED-2001 | 40.5 | 2.5 |

Suitable foams have also been prepared by combining these amine-terminated poly(alkylene oxides) with a polyoxypropylene amine sold by the Texaco Chemical Company under the name Jeffamine T-403 and having the following formula:

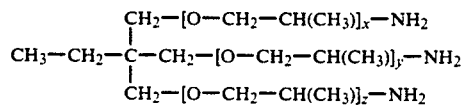

wherein the sum of x and y and z is between about 5 and about 7.3. It will be appreciated that such polyoxypropylene amines are also amine-terminated poly(alkylene oxides). The terminal amine groups may be mono-substituted with lower alkyl groups, preferably methyl and/or ethyl groups. However, these amine groups must have at least one hydrogen available for reaction in order to be useful in the copolymers of this invention.

Polyfunctional aliphatic amines are also incorporated into the hydrophilic polymers of this invention. Certain polyfunctional aliphatic amines have the general formula:

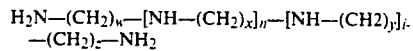

wherein w, x, y and z are independently selected to be the same or different and have a value of from 2 to about 15, and n and i are independently selected to be the same or different and have a value of from zero to about 6. More preferred are the difunctional amines having the formula:

as well as the trifunctional amines having the formula:

wherein x and y and independently selected to be the same or different and have a value of from 2 to about 15, such as, for example, ethylene diamine, butylene diamine, hexamethylene diamine, diethylene triamine, dihexamethylene triamine, and 2-methyl pentamethylene diamine, which is commercially available from DuPont as Dytek A.

The proportions of epoxy resin to amine-terminated poly(alkylene oxide) in the reaction mixture may vary over a substantial range. Preferably, the ratio of epoxy groups to amine groups (inclusive of the amine groups in both the polyfunctional aliphatic amines and the amine-terminated poly(alkylene oxide) portions of the reaction mixture) may range from about 1 to about 3. More preferably, this ratio is between about 1.5 and about 2.0 epoxy groups per amine group.

Polyfunctional aliphatic amines should be added to the reaction mixture such that they constitute from about 1% to about 12% by weight of the final polymer and, more preferably, from about 3% to about 8% by weight of the polymer. Thus, the addition of even a small amount of polyfunctional aliphatic amine results in a marked difference in the properties of the foam end product of this invention. Even the addition of about 3% by weight of polyfunctional aliphatic amine has produced a foam having lower density, increased strength and absorbency in comparison with a foam without polyfunctional aliphatic amine.

As noted, the provided hydrophilic materials find numerous applications in the form of foams and films. For example, the hydrophilic foams of this invention may be employed as absorbent elements in sanitary napkins such as disclosed in U.S. Pat. No. 4,759,754 in the name of Korpman, which is incorporated herein by reference.

The production of foams according to this invention is best carried out using a two step process consisting of first performing an intermediate reaction step and then foaming the reaction mixture as polymerization continues. This process is described in part in U.S. Pat. No. 4,554,297, which is incorporated herein by reference. The process there disclosed was modified in accordance with this invention to improve the reproducibility of the foams of this invention.

Foams according to the present invention were prepared as follows: excess epoxy resin was reacted with one or more amine-terminated poly(alkylene oxides) at a temperature between about 50° C. and 110° C. to produce a stable, viscous epoxy-terminated prepolymer denominated Part A. This reaction is complete within about 2 days if maintained at 50° C. and about 90 minutes if maintained at 110° C. Part A continued to react until its viscosity has about 850 centipoise. Additional amine-terminated poly(alkylene oxide) and polyfunctional aliphatic amine was combined with blowing agent to create Part B. Part B was maintained at room temperature. Part B was then combined with Part A (having a temperature between about 90° C. to about 110° C.) at room temperature and under good mixing conditions. The resulting mixture had a temperature of about 70° C. Simultaneously, the amine cured the epoxy and solidified and released gas, causing the mixture to foam. Upon mixing of the two components, foaming began and the creamy mass was cured in an oven held at 130° C. until a tack-free surface was obtained.

Those skilled in the art will recognize that blowing agents are alternatively known as foaming agents. A wide variety of blowing agents may be employed in the process of this invention. Certain preferred blowing agents, such as azo bis(isobutyronitrile) and benzene sulfonyl hydrazide, release gas upon heating. Other preferred blowing agents, such as sodium carbonate or sodium bicarbonate, release gas upon the addition of another chemical moiety, such as an acid or an acid salt. A particularly preferred blowing agent is sodium borohydride, which generates hydrogen gas upon heating in the presence of water.

The blowing agent should be introduced into the mixture at the appropriate time, i.e. when the viscosity of Part A is about 850 centipoise.

If the blowing agent is introduced too early into the prepolymer, the gas diffuses through the relatively liquid mixture and fails to form stable cells. If the blowing agent is introduced too late, the prepolymer will be too solid and inelastic for the gas to form cells.

According to this invention, the blowing agent should be mixed with one or more polyfunctional aliphatic amines and one or more amine-terminated poly(alkylene oxides) to yield Part B, which optionally comprises other additives, such as water and/or surfactant. Pluronic L-62, which is commercially available from BASF or other nonionic surfactants known to those of skill in the art may be used.

Foams according to the present invention and the prior art were prepared and characterized to demonstrate the significant improvements in properties and processing which attend the incorporation of small amounts of aliphatic amines in the polymers of the present invention. The results are summarized in Table I, wherein the following procedures were employed in characterizing the samples:

Density: 5"×5"×1" samples were cut and weighed. The density was calculated from the known weight and volume.

Cure Time: After mixing all the ingredients, the foam is allowed to rise and the time required to attain tack-free surface at 130° C. was measured.

Tensile Strength: 1"×5"×¼" strips were cut and pulled in an Instron testing device. Jaw separation was 3". Crosshead speed was 1" per minute.

Fluid Wicking Capacity: 1"×6"×¼" strips were prepared and placed on an incline at a specified angle (15° or 30°). The tip of each sample was dipped in a 1% NaCl solution and the fluid was allowed to wick into the sample until equilibrium was reached. This test reflects the ability of the foam to absorb and transport fluid spontaneously. The results are reported as amount of fluid per one gram of foam.

TABLE I

|  | 1 | 2 | 3 | 4 | 5 |
|---|---|---|---|---|---|
| Part A (90° C.) | | | | | |
| EPON 828, gr | 46 | 52.3 | 59 | 57 | 60 |
| Jeffamine ED-600, gr | 6 | 14.6 | 8 | 7.1 | 16.6 |
| Jeffamine ED-2001, gr | 20 | — | 26 | 25 | — |
| Part B (20° C.) | | | | | |
| 2-Methyl Pentamethylene Diamine, gr | — | — | 7 | 5.8 | 3.4 |
| Jeffamine ED-600, gr | 28 | 33.1 | 0 | 5 | 20 |
| Sodium Borohydride, gr | 0.75 | 0.75 | 0.75 | 0.75 | 0.75 |
| Pluronic L-62, gr | 1.0 | 1.0 | 1.0 | 1.0 | 1.0 |
| Water, gr | 2.0 | 2.0 | 2.0 | 2.0 | 2.0 |
| Properties | | | | | |
| Density lb/ft$^3$ | 4.5 | 4.1 | 2.5 | 2.8 | 3.0 |
| Cure Time, min. at 130/C. | 9.0 | 8.0 | 2.0 | 2.0 | 3.0 |
| Tensile Strength, PSI | | | | | |
| Dry | 1.27 | 1.9 | 13.0 | 9.2 | 9.8 |
| Wet | 0.6 | 0.7 | 5.4 | 2.4 | 3.11 |
| Fluid Wicking Capacity, g/g | | | | | |
| 15° | 4.6 | 2.7 | 17.0 | 13.2 | 10.4 |
| 30° | 2.7 | 1.8 | 10.1 | 8.1 | 7.5 |

The results summarized in Table I clearly demonstrate the improvements in foam properties and processability which resulted from the addition of 2-methyl pentamethylene diamine. Samples 1 and 2 illustrate foams without the poly-aliphatic diamine 2-methyl pentamethelene diamine have considerably higher density, longer cure time, lower wet and dry tensile strength and much lower fluid wicking capacity than foams containing 2-methyl pentamethylene diamine. The lower density and shorter cure time make the formulations of this invention more economic to make in that they can be processed more quickly. Moreover, the same amount of materials can create a larger volume of foam than that of the prior formulations.

In principle, hydrophilic films can also be prepared according to the present invention by omitting the blowing agent and the water from the formulations.

Thus, films according to this invention are prepared by reacting one or more amine-terminated poly(alkylene oxides) with excess epoxy resin at a temperature between about 50° C. and 110° C. to produce a stable, viscous prepolymer. As the reaction proceeds and polymerization occurs between the epoxy resin and amine-terminated poly(alkylene oxide), the viscosity of the prepolymer rises. The viscous oligomer is then cooled to 25° C. and diluted to a 50% (weight) solution with isopropyl alcohol or some other suitable solvent.

One or more polyfunctional aliphatic amines are then mixed with one or more amine-terminated poly(alkylene oxides) and, optionally, other additives such as the surfactant Pluronic L-62. This blend is then mixed with the prepolymer to produce a viscous reaction mixture, which is allowed to reach room temperature.

To produce a hydrophilic film, an approximately 10 mil thick film of the viscous reaction mixture is drawn on a glass plate that is pretreated with a mold release such as silicone or a fluorocarbon. The alcohol/solvent is allowed to evaporate for about 30 minutes at room temperature and the coated plate is placed in a 100° C. hot air oven for about 20/minutes until the film cures. The cured hydrophilic film is then removed from the glass.

What is claimed is:

1. A hydrophilic material comprising the reaction product of a reaction mixture which comprises at least one epoxy resin, at least one amine-terminated poly(alkylene oxide), and at least one polyfunctional aliphatic amine.

2. The hydrophilic material of claim 1 wherein the epoxy resin has an average of at least 1.7 epoxy groups per resin molecule.

3. The hydrophilic material of claim 1 wherein the epoxy resin has an average of between about 1.7 and about 4.0 epoxy groups per resin molecule.

4. The hydrophilic material of claim 1 wherein the epoxy resin comprises a polyglycidyl ester of a polycarboxylic acid.

5. The hydrophilic material of claim 1 wherein the epoxy resin comprises a glycidyl ether resin.

6. The hydrophilic material of claim 1 wherein the epoxy resin comprises an alkanediol glycidyl ether having the formula:

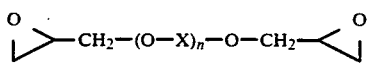

wherein X is selected from the group consisting of alkylene and alkylidene groups containing from 1 to about 10 carbon atoms, and n has a value of from 1 to about 25.

7. The hydrophilic material of claim 1 wherein the epoxy resin is selected from the group consisting of di- and polyglycidyl ethers of bisphenols, the bisphenols having the formula:

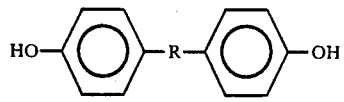

wherein R is a bivalent radical comprising from 1 to about 8 atoms selected from the group consisting of C, O, S, or N.

8. The hydrophilic material of claim 7 wherein R is selected from the group consisting of alkylene and alkylidene radicals containing from 1 to about 8 carbon atoms.

9. The hydrophilic material of claim 1 wherein the epoxy resin comprises isopropylidene bisphenol.

10. The hydrophilic material of claim 1 wherein the amine-terminated poly(alkylene oxide) is selected from the group consisting of amine-terminated poly(propylene oxide), amine- terminated poly(ethylene oxide), amine-terminated copolymers of ethylene oxide and propylene oxide, and mixtures thereof.

11. The hydrophilic material of claim 10 wherein the ratio of ethylene oxide groups to propylene oxide groups in the amine-terminated poly(alkylene oxide) is between about 1 and about 15.

12. The hydrophilic material of claim 10 wherein the ratio of ethylene oxide groups to propylene oxide groups in the amine-terminated poly(alkylene oxide) is between about 3 and about 10.

13. The hydrophilic material of claim 1 wherein the reaction mixture comprises from about 1 to about 3 epoxy groups per amine group.

14. The hydrophilic material of claim 1 wherein the reaction mixture comprises from about 1.5 to about 2.0 epoxy groups per amine group.

15. The hydrophilic material of claim 1 wherein the amine-terminated poly(alkylene oxide) comprises a compound having the formula:

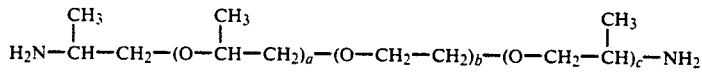

wherein b has a value of from about 8 to about 50 and the sum of a and c has a value of from about 1 to about 5.

16. The hydrophilic material of claim 1 wherein the amine-terminated poly(alkylene oxide) comprises a compound having the formula:

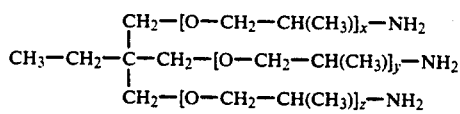

wherein the sum of x and y and z is between about 5 and about 10.

17. The hydrophilic material of claim 1 wherein the polyfunctional aliphatic amine comprises a compound selected from the group consisting of ethylene diamine, butylene diamine, hexamethylene diamine, 2-methyl pentamethylene diamine, diethylene triamine, and dihexamethylene triamine.

18. The hydrophilic material of claim 1 wherein the polyfunctional aliphatic amine comprises a compound having the formula:

$$H_2N-(CH_2)_x-NH_2$$

wherein x has a value of from 1 to about 15.

19. The hydrophilic material of claim 1 wherein the polyfunctional aliphatic amine comprises a compound having the formula:

$$H_2N-(CH_2)_x-NH-(CH_2)_y-NH_2$$

wherein x and y are independently selected to be the same or different and have a value of from 1 to about 15.

20. The hydrophilic material of claim 1 wherein the polyfunctional aliphatic amine comprises a compound having the formula:

$$H_2N-(CH_2)_w-[NH-(CH_2)_x]_n-[NH-(CH2)_y]_i-(CH_2)_z-NH_2$$

wherein w, x, y and z are independently selected to be the same or different and have a value of from 2 to about 15, and n and i are independently selected to be the same or different and have a value of from zero to about 6.

21. The hydrophilic material of claim 1 wherein the reaction mixture comprises from about 1% to about 12% polyfunctional aliphatic amine by weight.

22. The hydrophilic material of claim 1 wherein the reaction mixture comprises from about 3% to about 8% polyfunctional aliphatic amine by weight.

23. The hydrophilic material of claim 1 wherein the reaction mixture further comprises a blowing agent.

24. The hydrophilic material of claim 23 wherein the blowing agent is sodium borohydride.

25. The hydrophilic material of claim 1 wherein the reaction mixture further comprises a surfactant.

26. The hydrophilic material of claim 1 wherein the material is in the form of a foam.

27. The hydrophilic material of claim 1 wherein the material is in the form of a film.

28. A product which is useful in absorbing bodily fluids, comprising a hydrophilic foam which comprises the reaction product of a reaction mixture which comprises at least one epoxy resin, at least one amine-terminated poly(alkylene oxide), and at least one polyfunctional aliphatic amine.

29. A sanitary napkin comprising a hydrophilic foam which comprises the reaction product of a reaction mixture which comprises at least one epoxy resin, at least one amine-terminated poly(alkylene oxide), and at least one polyfunctional aliphatic amine.

30. A method for preparing hydrophilic materials comprising the steps of:
   providing at least one epoxy resin;
   forming a reaction mixture by contacting the epoxy resin with at least one amine-terminated poly(alkylene oxide) and at least one polyfunctional aliphatic amine; and
   curing the reaction mixture.

31. A method for preparing hydrophilic materials comprising the steps of:
   providing at least one epoxy resin;
   forming a prepolymer by contacting excess epoxy resin with at least one amine-terminated poly(alkylene oxide);
   forming a reaction mixture by contacting the prepolymer with at least one amine-terminated poly(alkylene oxide) and at least one polyfunctional aliphatic amine;
   curing the reaction mixture.

32. A method for preparing hydrophilic foam comprising the steps of:
   providing at least one epoxy resin;
   forming a prepolymer by contacting excess epoxy resin with at least one amine-terminated poly(alkylene oxide);
   forming a foaming mixture by contacting the prepolymer with at least one amine-terminated poly(alkylene oxide), at least one polyfunctional aliphatic amine, and a blowing agent;
   curing the foaming mixture.

* * * * *